United States Patent [19]
Errico et al.

[11] Patent Number: 5,899,904
[45] Date of Patent: May 4, 1999

[54] COMPRESSION LOCKING VERTEBRAL BODY SCREW, STAPLE, AND ROD ASSEMBLY

[75] Inventors: Joseph P. Errico, Far Hills; Thomas J. Errico, Summit; James D. Ralph, Oakland, all of N.J.

[73] Assignee: Third Milennium Engineering, LLC, Summit, N.J.

[21] Appl. No.: 09/174,959

[22] Filed: Oct. 19, 1998

[51] Int. Cl.$^6$ ...................................................... A61B 17/70
[52] U.S. Cl. ................................. 606/61; 606/73; 606/75; 606/69
[58] Field of Search ................................ 606/60, 61, 69, 606/70, 72, 73, 75

[56] References Cited

U.S. PATENT DOCUMENTS

| | | | |
|---|---|---|---|
| 5,415,659 | 5/1995 | Lee et al. | 606/61 |
| 5,620,443 | 4/1997 | Gertzbein et al. | 606/73 |
| 5,662,652 | 9/1997 | Schafer et al. | 606/73 |
| 5,690,629 | 11/1997 | Asher et al. | 606/75 |
| 5,713,898 | 2/1998 | Stucker et al. | 606/61 |
| 5,810,816 | 9/1998 | Roussouly et al. | 606/61 |

Primary Examiner—Michael Buiz
Assistant Examiner—Daphna Shai
Attorney, Agent, or Firm—Joseph P. Errico, Esq.

[57] ABSTRACT

A rod, screw, rod securing member, and staple assembly for use in conjunction with anterior or lateral spinal rod implant apparatus includes a vertebral body screw and rod coupling member which are loosely coupled by virtue of the head of the screw being held within a contractible volume in the base of the rod coupling member. The volume of the rod coupling member is contractible by virtue of a series of slots formed in the base, which also has a tapered exterior surface. The staple includes a flat portion which has a hole through it and several barbs extending downward from it for gripping the surface of the vertebral bone. The hole in the staple has a rim which is upwardly extending and a tapered interior side wall designed to engage the tapered exterior wall of the rod coupling member such that advancement of the staple relative to the coupling member causes the interior volume to compression lock to the head of the screw. The screw, with the rod coupling element mounted thereto, is first inserted into the vertebral bone, and then the staple is mounted over the rod coupling member. The member is rotated into position to receive the rod, which seats on the uppermost surface of the annular rim of the hole in the staple. The application of a top locking nut causes the rod to compress against the staple, the barbs of which are driven into the vertebral bone, the rod coupling element and the screw to be locked, and the staple and the screw/member combination are securely locked together.

7 Claims, 3 Drawing Sheets

COMPRESSION LOCKING VERTEBRAL BODY SCREW, STAPLE, AND ROD ASSEMBLY

BACKGROUND OF THE INVENTION

1. Field of the Invention

This invention relates generally to a spinal rod fixation apparatus having an elongate rod, a vertebral body screw, and a stabilizing staple element, and more particularly to a rod, screw and staple assembly having a rotateable screw head which is selectively lockable in combination with the rod and staple to provide enhanced stability and bone holding strength.

2. Description of the Prior Art

The spinal column is highly complex system of bones and connective tissues which houses and protects critical elements of the nervous system and the arterial and veinous bodies in close proximity thereto. In spite of these complexities, the spine is a highly flexible structure, capable of a high degree of curvature and twist through a wide range of motion.

Genetic or developmental irregularities, trauma, chronic stress, tumors, and disease, however, can result in spinal pathologies which either limit this range of motion, or which threaten the critical elements of the nervous system housed within the spinal column. A variety of mechanical implant structures have been disclosed in the art which are used during surgical intervention to immobilize segments of the spine which are either unstable or have, in combination, become so irregular that they threaten the continued health of the patient. These assemblies are generally classified as anterior, posterior, or lateral. As the classifications suggest, posterior implants are attached to the back of the spinal column, generally hooking under the lamina and entering into the central canal, attaching to the transverse process, or coupling through the pedicle bone using pedicle screws. Posterior fixation assemblies using such screws are generally used in short sequence immobilization indications, and generally in the larger, lower lumbar bones, for their attending pathologies. Lateral and anterior assemblies, by contrast are coupled to the anterior portion of the spine, which is the sequence of vertebral bodies, and are often used throughout long segments of lumbar and thoracic sequences of vertebrae. A specific pathology which often requires significant surgical intervention along extended numbers of vertebrae is scoliosis. The present invention relates to spinal fixation devices for immobilizing and altering the alignment of the spine over a large number, for example more than three or four, vertebra by means of affixing at least one elongate rod to the sequence of selected vertebral bodies.

Anterior (and/or lateral) "rod assemblies" of the prior art have generally been inserted into the bone either unicortically or bicortically, wherein the shaft of the screw transects (and gains fixation strength as it passes through) one or two exterior layers of the vertebral bone, respectively. Exposing the tip of the screw shaft through the opposing side of the bone's exterior surface does, however, entail a risk inasmuch as important blood vessels, nerve roots, as well as other critical tissues are often in jeopardy of injury through contact with an exposed screw tip. Bicortical fixation, however, provides greatly enhanced strength against pullout; an event in which the screw is pulled free of the bone as its grip inside the vertebra fails to hold.

In order to provide enhanced stability against such pullout events, a staple as shown in FIG. 1, was designed. The basic staple of the prior art comprises a flat metal surface 10 having a hole 12 formed in the center thereof. The corners 14 of the staple 10 are curved downwardly to form four spaced apart spikes. The basic vertebral body screw 20, rod 30 and top locking nut 40 of the prior art are shown in FIG. 2, in conjuction with the staple 10, in an exploded assembly diagram. The screw 20 is inserted through the hole 12 in the staple 10 until the wider top, rod receiving portion 22 of the screw, contacts and seats in the hole 12 of the staple. The wider base, provided by the staple 10, impairs toggling action by the screw within the bone, and is intended to prevent motion which can cause the screw to bone interface from breaking down. The rod 30 is then placed in the rod receiving channel 24 of the screw head 22, and a top locking nut 40 is advanced onto the top of the screw head 22, thereby locking the rod to the screw 20, and by association, to the bone.

In some advanced embodiments of this screw and staple design (not shown), the hole and the bottom of the screw are designed such that the screw may be inserted at a modest angle to the staple, thus permitting stable seating of the screw and staple, despite slight offsets of the screw relative to the bone surface.

These screw and staple assemblies of the prior are, however, do not prevent the most frequent pullout failure mechanism, which is direct vertical force pullout which is caused when the rod itself imparts a sufficient stress against the shaft to cause the screw to back out of the hole. In addition, the ability of the staple to impair toggling of the screw in the bone is limited insofar as the screw and staple are not held together by any specific means, and theerfore does not prevent the screw from rotating in the hole and causing microfractures, which can lead to bone failure. Further, the prior art designs limit the ability of the rod receiving head of the screw to be properly aligned with the rod. In many instances, the screw is not fully seated in the hole of the staple because the screw had to be backed out of the hole by the surgeon to align the rod in the rod receiving channel of the head. In such fixed head screw designs, the alignment of the rod receiving channel of the head is not independent of the height of the screw insofar as the rotation of the head causes the threading of the screw to rise up from or dig deeper into the bone. This creates a substantial difficulty for surgeons as they try to seat the rod properly into the screw head while simultaneously having the screw head seat in the hole in the staple.

It is, therefore, the principal object of the present invention to provide a vertebral body screw, rod, and staple assembly which provides enhanced stability and pullout protection.

In addition, it is an object of the present invention to provide such an assembly which includes a stable locking of the staple to the screw so that the screw head can be positioned in the ideal orientation without risking the union of the screw and staple.

It is a related object of the present invention to introduce a screw having a head which may be independently rotated relative to the shaft of the screw, but which may be securely locked in the desired orientation when combined with the screw and staple.

Accordingly it is also an object of the present invention to provide an assembly in which the staple and screw are lockably coupled together upon completion of the implantation.

It is also a principal object of the present invention to provide a reliable, durable, and efficient, long term fixation assembly for spine stabilization.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a vertebral body staple, screw and rod assembly, having enhanced stability and pullout strength, in which the staple, the rod and the screw may be locked together to form a reliable fixation to the vertebral bone. More particularly, the assembly of the present invention comprises a vertebral body screw having a shaft and head portion and a rod receiving member which is rotationally mounted hereto. The head of the screw is rounded and is designed to fit inside a recessed volume in the base of the rod receiving member. In the preferred embodiment, the head comprises a frustoconical section. The recessed volume of the rod receiving member is correspondingly shaped to receive, and retain therein, the head portion of the screw. The walls of the base of the rod receiving member which define this recessed volume are vertically slotted such that the head of the screw may be loosely or rigidly maintained therein in accordance with the application of an external pressure applied to the base portion. In the uncompressed state, the rod receiving member floats on the head in such a way that the head may be selectively rotated independently from the shaft portion of the screw. The upper portion of the rod receiving member is formed with a channel, for receiving the rod, and a locking means (for example a threading) for engaging a locking element (for example a nut or set screw) which secures the rod in the rod receiving channel. The present invention also includes a vertebral body staple which engages the vertebral bone, the rod, and the rod receiving member in such a way that the action of locking the rod in the rod receiving channel further causes the base portion of the rod receiving member to compress against the head of the screw and secure the assembly in a rigid position.

Referring specifically to the vertebral body screw of the present invention, the screw comprises a shaft and a head. The shaft portion of the screw is designed to be inserted into the vertebral bone, and to firmly anchor the screw to the bone. This fixation is generally enhanced by the shaft including a threading which engages the bone material along its length and prevents axial translation of the shaft along the length of the hole in the bone into which it has been advanced. The head of the screw is rounded, and, as stated above, is preferrably a frustoconical section. More particularly, the head of the screw may curvately or linearly tapered in the axial direction, but should comprise a circular transverse cross section, such that when the head is retained in a similarly shaped volume of the rod receiving member (as more fully described hereinbelow), the shaft and the head may rotate independently from the rod receiving member.

The rod receiving member of the assembly includes an upper portion and a base portion. The base portion comprises a recessed interior volume which is shaped to receive the head of the screw. More specifically, the volume is shaped to receive and retain the head of the screw by expanding to receive the head, and then contracting around it once it has been fully inserted. This expanding and contracting action of the recessed volume is provided by a series of vertical slots formed in the base portion which permit expansion and contraction of the volume in accordance with the application of an applied force (such as the forcible advancement of the head of the screw portion thereinto). The exterior surface of this base portion is also tapered outwardly (preferably linearly) such that the lowermost portion of the base has a greater diameter than the upper portion of the rod receiving member. This tapered surface comprises an engaging surface against which a force may be applied to compress the interior volume. The action and actuation of this volume by applying a pressure against the engaging surface shall be explained in greater detail with respect to the assembly of the screw, rod receiving member, and the staple.

The upper portion of the rod receiving member comprises a channel for receiving a rod, which channel may alternatively be formed vertically, descending down from the top of the member, or laterally, coming in from the side of the member. More particularly, both types of rod receiving channel admit the rod into the member such that the rod extends perpendicularly to the overall vertical axis of the member, but in the first instance (the vertical channel), the channel is formed between two upright extending arms, and in the second (the lateral channel), the channel is formed in the side of the member. In each embodiment, the upper portion of the member (either the upper portion of the upright extending arms or the portion of the member directly above the lateral channel) includes a threading for receiving thereon a top locking nut, or other means for securing a rod within the channel.

The vertebral body staple comprises a member having a flat portion and a plurality of downwardly directed protuberances, generally shaped like spikes or barbs, which extend perpendicularly to the plane formed by the flat portion. The flat portion further includes a hole formed in the center thereof. The hole has an upwardly extended exterior rim and is shaped such that the hole has a cylindrical appearance. More particularly, the cylindrical hole in the staple is tapered in correspondence with the taper of the base portion of the rod receiving member. It is further of the appropriate diameter to seat around the base of the rod receiving member, so that it may nest against the engaging surfaces of the base.

Functionally, the head of the screw is inserted into the base of the rod receiving member such that the two elements are loosely coupled and may rotate freely and independently about a common axis. The upper portion of the rod receiving member may be inserted through the hole in the staple. The tapered exterior surface of the base of the rod receiving member and the tapered interior of the hole in the staple are designed to nest. The upwardly extending rim portion of the staple is designed to seat above the deepest surface of the rod receiving channel such that a rod placed in the channel rests on the upper surface of the rim, and not on the lowermost surface of the channel. Locking of the rod in the channel by means of a nut or set screw(engaging the locking means of the upper portion of the rod reciving member) causes the staple to translate downwardly along the exterior surface of the base, causing a compression of the interior volume, and a compression locking of the screw head to the interior surface of the recessed volume.

The surgical assembly of the present invention is provided as follows. First, the vertebral body surfaces are exposed and prepared to receive the screws (one at each bone). The screws are advanced into the bones at the appropriate angles and to the desired height. The rod receiving members may be placed on the heads of the screws prior to the insertion, i.e. in the surgical environment, or prior to insertion. If the rod receiving members and the screws are coupled prior to insertion of the screw, the interior volume of the base must include a hole through which the surgeon may insert a screw driving tool to engage and apply an advancing torque to the screw. As this embodiment and assembly is preferred, a suitable recess and hole in the head of the screw and the rod receiving member, respectively, are suggested. Such features should be coaxial.

Once the screw and the rod receiving member have been inserted into the bone, the rod receiving member is rotated into the appropriate alignment to receive the rod. Prior to inserting the rod, however, the staples are then placed over the rod receiving members such that the upper portions of the members extend through the holes in the staples, and the upwardly extending rims of the holes are positioned above the lowermost surfaces of the channels. The barbs of the staples should be driven into the bone as deeply as possible without forcibly locking the screw and rod receiving member together. The rod is then placed into the channels of the members, extending along the length of the spinal sequence which is to be immobilized. The locking means, for example a locking nut, is then advanced onto the engaging means of each of the rod receiving members to secure the rod in the channel. The advancement of the rod into the channel by the locking nut, or other such means, causes the staple to be pushed downward further along the exterior surface of the base portion of the rod receiving member, while simultaneously having its barbs further advanced into the bone. The compressive force of the nut against the rod, the rod against the staple, the staple against the tapered exterior of the base of the rod receiving member, and the member against the head of the screw firmly locks the assembly together and to the vertebral bone.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 1:
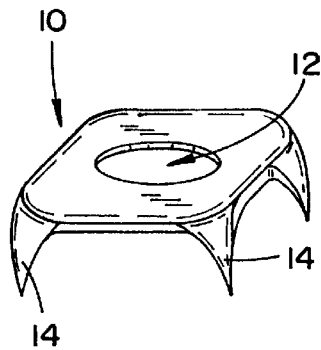
FIG. 1 is a side perspective view of a vertebral body staple of the prior art.
Figure 2:
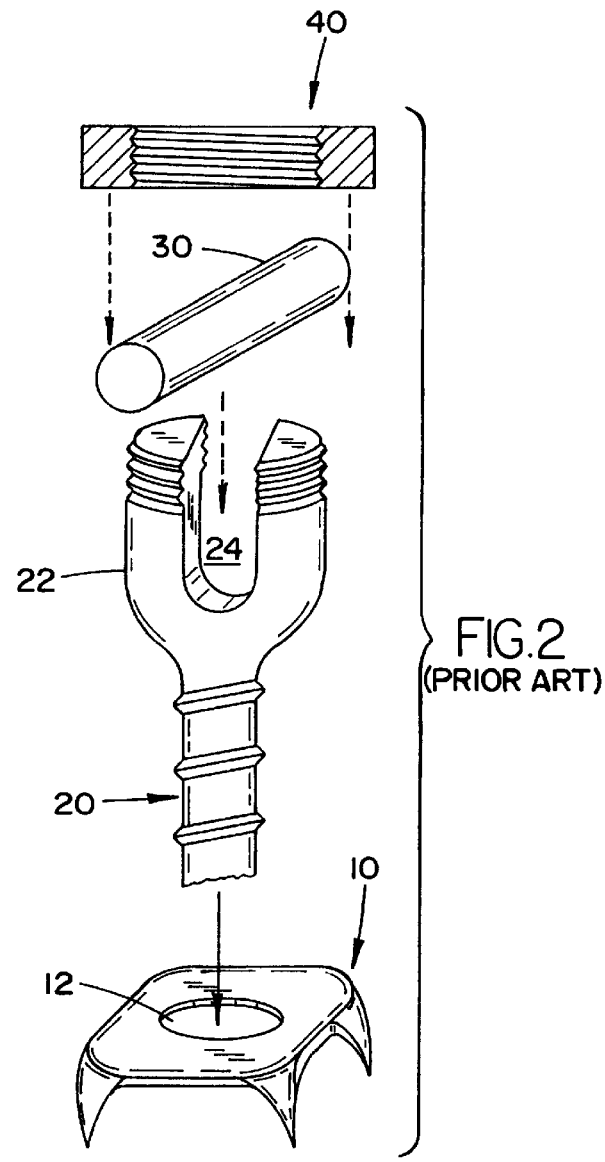
FIG. 2 is an exploded assembly view of a staple, vertebral body screw, rod and top locking nut of the prior art.
Figure 3:
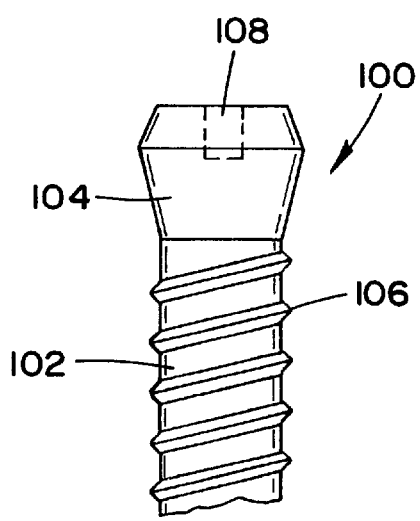
FIG. 3 is a side view of a vertebral body screw which is an aspect of the present invention.

Referring now to FIG. 3, a side view of a vertebral body screw 100 of the present invention, comprising a shaft and a rod coupling head, is shown. The screw 100 comprises a shaft 102, which is threaded, and a head portion 104 having a frustoconical shape. The threading 106 of the shaft 102 is preferably of the type which is suited for high engagement with bone materials, as are well known in the art. It shall be understood that a variety of shaft designs are interchangeable with the present design. The specific choice of shaft features, such as thread pitch, shaft diameter to thread diameter ratio, and overall shaft shape, should be made be the physician with respect to the conditions of the individual patient's bone, however, this invention is compatible with a wide variety of shaft designs.

The head 104 of the screw 100 is round, and, as stated above, is preferably a frustoconical section. A recess 108 is formed in the top of the head 104 so that the screw may be engaged by a torque applying instrument, and thereby be advanced into the vertebral bone. While it shall be understood that the head may curvately or linearly tapered in the axial direction, it should comprise a circular transverse cross section, such that when the head is retained in a similarly shaped volume of the rod receiving member (as more fully described hereinbelow with reference to FIG. 4), the shaft and the head may rotate independently from the rod receiving member.

Figure 4:
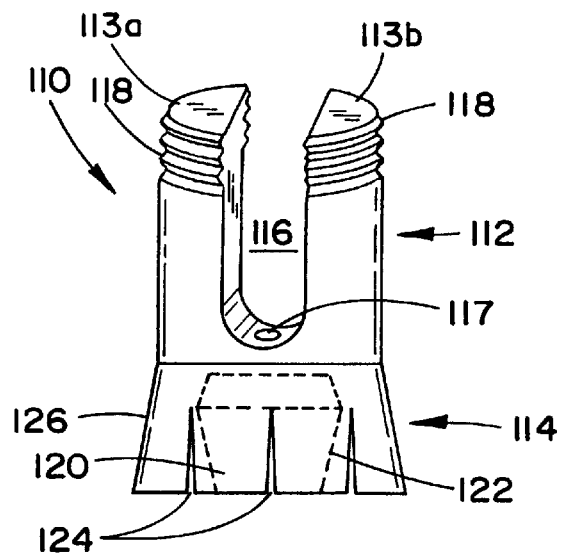
FIG. 4 is a side view of a rod receiving member which is an aspect of the present invention, in which interior features of the member are also shown.

Referring now to FIG. 4, the rod receiving member 110 of the present invention is provided in a side perspective view. The member 110 may be conceptually divided into an upper and lower portions 112 and 114, respectively. The upper portion 112 of the member comprises a pair of upwardly extending arms 113a,113b which define therebetween a rod receiving channel 116. The uppermost exterior surfaces of the upwardly extending members 113a,113b include a threading 118 which is ideally suited for receiving a locking nut (as set forth more particularly with respect to FIG. 6). In alternative designs (not shown), which were introduced above, it is possible to design the rod receiving channel 116 into the side of the upper portion 112, however, the preferred embodiment includes the rod receiving channel 116 in a vertical alignment.

The lower portion 114 of the rod receiving member 110 comprises cylindrical body having a recessed interior volume 120 which is shaped to receive the head 104 of the screw 100, i.e., it has a frustcorical interior side wall 122. More specifically, the shape of the head 104 and the volume 120 are designed to mutually engage one another such that the head of the screw is retained within the interior volume 120. This retention is achieved by allowing the volume 120 to first expand to receive the head, and then to contract around the head 104 once it has been fully inserted. This expanding and contracting action of the volume 120 is enabled by a series of vertical slots 124 formed in the base 114 which permit expansion and contraction of the volume 120 in accordance with the application of an applied force.

The exterior surface 126 of the lower portion 114 is also tapered outwardly (preferably linearly) such that the lowermost portion of the base has a greater diameter than the upper portion 112 of the rod receiving member. This tapered surface comprises an engaging surface 126 against which a force may be applied to compress the interior volume 120. The expansion of the volume is achieved by forcible insertion of the head 104 of the screw 100 into the volume 120, and it is contracted by applying a pressure against the engaging surface 126.

Figure 5:
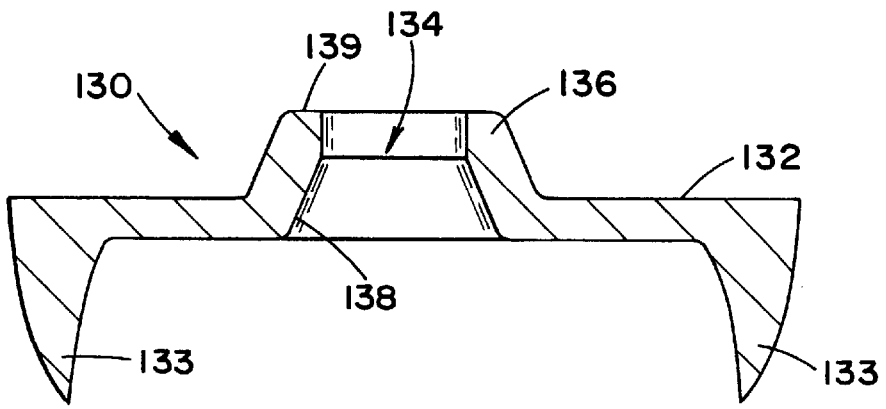
FIG. 5 is a side cross-sectional view of a vertebral body staple which is an aspect of the present invention.

Referring now also to FIG. 5, the vertebral body staple 130 of the present invention is provided in a side cross section view. The staple 130 includes a flat surface 132 and a plurality of downwardly directed barbs 133, disposed at the lateral edges of the flat portion 132. The barbs 133, which are intended to be inserted into the vertebral bone surface to provide fixation of the staple to the bone, extend perpendicularly downward from the plane formed by the flat portion 132. The flat portion 132 further includes a hole 134 formed in the center thereof. The hole 134 has a cylindrical rim 136 which extends upwardly from the flat surface to an uppermost annular surface 139. This upwardly extending annular rim 136 has an inner surface 138 which is tapered along its length, which is ideally suited to engaging the tapered exterior surface 126 of the rod receiving member 110.

Figure 6:
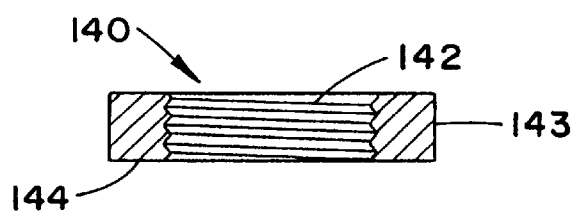
FIG. 6 is a side cross-section view of a top locking nut which is an aspect of the present invention.

Referring now to FIG. 6, a top locking nut 140 of the present invention is provided in a side cross section view. The nut 140 comprises a standard threaded nut design, having an interior threading 142 which is matable and advanceable along the exterior threading 118 of the upper portion 112 of the rod receiving member 110. The exterior surface 143 of the nut 140 is ideally suited for engagement and advancement along this threading 118 by means of a standard torque applying instrument, such as having a series of flats for engaging a wrench or socket. The lower surface 144 of the nut 140 is flat, thus providing maximal surface area over which the downward locking force applied by the nut may be borne.

Figure 7:
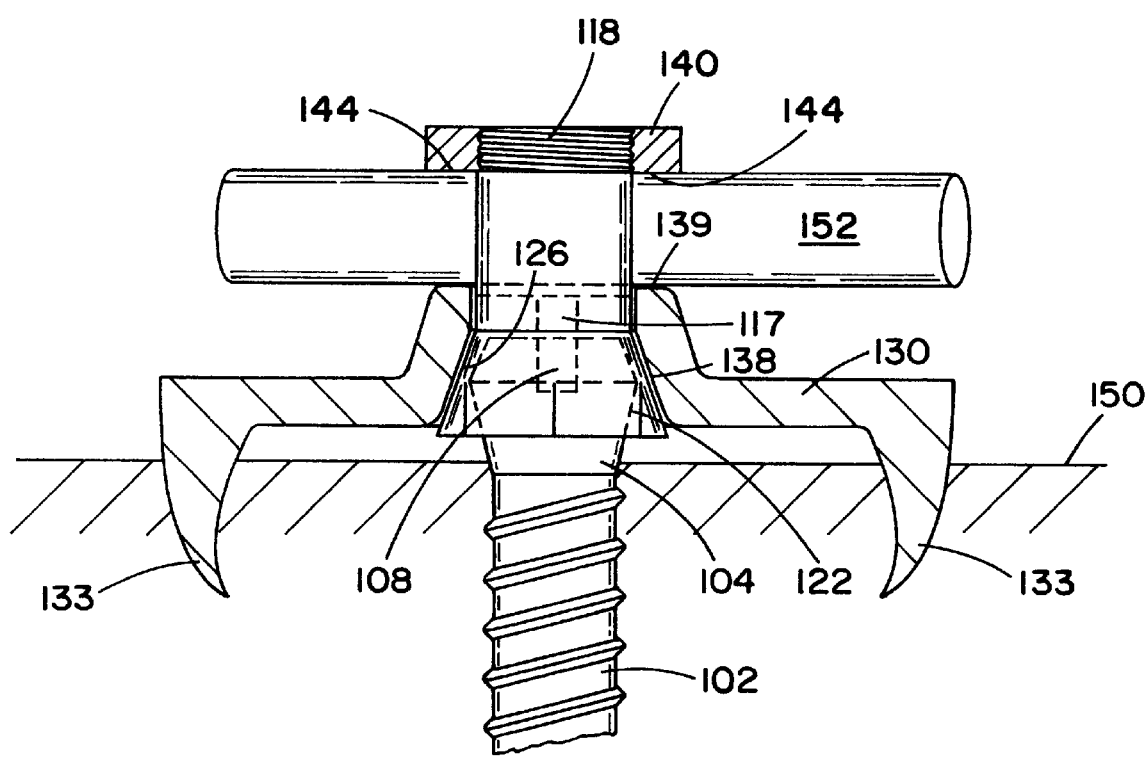
FIG. 7 is a side cross section view of a fully assembled embodiment of the present invention.

Referring now to FIG. 7, a completely assembled embodiment of the present invention is provided in a side cross section view, this view being taken along a direction in which the rod receiving member 110 is rotated about its elongate axis by 90 degrees from the orientation illustrated in FIG. 4. The implantation of this device, as well as its functionality and advantages shall be explained in conjunction with the description of the elements and workings set forth in this FIG. 7. The screw 100 and the rod receiving member 110 are first coupled by inserting the head 104 of the screw into the interior volume 120 of the member 110. In this initial incarcerated state, the head and member may rotate independently about their common elngate axis, however neither element may be axially separated by virtue of the strong interference fit of the head 104 within the volume 120.

The recess 108 in the screw is then accessed through the hole 117 which is formed in the base of the rod receving channel 116 and the shaft 102 of the screw is driven into the vertebral bone such that the head 104 is exposed above the bone surface (hereinafter identified as 150). The rod receiving member 110 is then independently rotated into the appropriate orientation for receiving the rod 152. The staple 130 is then mounted over the rod receiving member 110 such that the upper portion 112 of the member extends through the hole 134 in the staple 130. The upper surface 139 of the annular rim 136 of the hole 134 will be positioned above the bottom of the rod receiving channel 116 (because the height of the rim is greater than the height of that portion of the member). The barbs 133 of the staple 130 are then inserted by force into the vertebral bone surface 150 as deeply as possible without causing the head and the member to be prematurely locked together.

Once the staple 130, rod receiving member 110, and screw 100 have been properly positioned, the rod 152 is inserted into the rod receiving channel 116, and seats against the upper surface 139 of the annular rim 136. The subsequent application of the top locking nut 140 onto the threading 118 of the upwardly extending arms 113a,113b, and it's advancement downwardly, causes several sinulataneous events to take place. First, the rod is compressed between nut and the annular rim, thereby locking the rod to the staple and the rod receiving member. Second, the pressure against the rod 152 by the lower surface 144 of the nut 140 applies a pressure against the staple 130, which further drives the barbs 133 deeper into the vertebral bone. Third, a compressive force is applied by the inner surface 138 of the hole 134 of the staple against the tapered engaging surface 126 of the member 110 causing the interior volume 120 to compress. And correspondingly, the head of the screw, which was previously loosely incarerated within the volume, is then locked securely within the volume by a compression lock of the inner surface 122 of the volume 120 against the head 104. Thus the staple 130, the rod 152, the screw 100, the rod reciving member 110, and the vertebral bone 150 are stably fixed together. This assembly strongly prevents screw pullout failure of the rod immobilization construct by providing a wider base of fixation strength for anchoring to the bone, as well as providing selective rotational freedom for the surgeon to align the rod with the channel, without risking a poor staple to screw interface.

While there have been described and illustrated embodiments of a rod, vertebral body screw and staple assembly for use with anterior or lateral spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A vertebral body screw and staple assembly for use with orthopedic rod implantation apparatus, comprising:

a vertebral body staple having first and second portions thereof, said first portion including means for direct fixation of the staple to vertebral bone, said second portion having a throughhole formed therein, said throughhole having a tapered interior sidewall;

a vertebral body screw having a shaft which is insertable into a vertebral bone and a head portion which includes a curvate portion;

a rod receiving member including an upper portion and a lower portion,
said upper portion including a rod receving channel,
said lower portion including an interior volume into which the head portion of the screw may be inserted, a tapered exterior surface having at least one slot formed therein such that said interior volume is selectively contractible by the application of a force against the tapered exterior surface;

means for securing a rod in said rod receiving channel;

said throughhole of said staple being mountable about the rod receiving member, such that the insertion of said screw into a vertebral bone, the insertion of the head of the screw into the interior volume of the rod receiving member, the mounting of the staple about the rod receiving member, the insertion of a rod in said rod receiving channel, and the application of said means for securing the rod in the rod receiving channel causes the interior volume of the rod receving member to compression lock to the head of the screw, the staple to be locked to the rod receiving member, and the rod to be locked to both the rod receiving member and the staple, thereby fully securing the assembly to the vertebral bone.

2. The vertebral body screw and staple assembly as set forth in claim 1, wherein said means for direct fixation of the staple to vertebral bone comprises a plurality of downwardly extending barbs.

3. The vertebral body screw and staple assembly as set forth in claim 1, wherein the second portion of the staple further comprises an annular rim around the throughhole formed, which annular rim is upwardly extending.

4. The vertebral body screw and staple assembly as set forth in claim 3, wherein the annular rim of the staple extends above a lowermost surface of the rod receiving channel, such that when the staple is mounted about the rod receiving member, and the rod is inserted into the rod receiving channel, the rod seats on an upper surface of the annular rim.

5. The vertebral body screw and staple assembly as set forth in claim 1, wherein said means for securing a rod in said rod receiving channel comprises a top locking nut which mates to a threading formed on the upper portion of the rod receiving member.

6. A vertebral body screw and staple assembly for use with orthopedic rod implantation apparatus, comprising:

a vertebral body staple having a portion thereof which is flat, said flat portion having an upper surface and a lower surface, said staple further having a plurality of vertebral bone fixation protuberances extending downwardly therefrom, said flat portion further including a throughhole formed therein which extends from the upper surface through the lower surface, said throughhole having an upwardly extending annular rim and a tapered interior surface;

first means for securing a rod in a rod receiving channel;

a vertebral body screw having a shaft portion and a curvate head portion a rod receiving member having an upper portion and a lower portion, said upper portion having a rod receiving channel formed therein which has a lower channel surface and second means formed thereon for receiving thereon said first means for securing said rod in said rod receiving channel, said upper portion being insertable through said throughhole of said staple from the lower surface, said lower portion of said rod receiving member having an interior volume and a tapered exterior surface, said interior volume being capable of receiving therein said head of said screw such that it is loosely retained such that the screw and the rod receiving member may rotate freely relative to one another, said tapered exterior surface including at least one slot formed therein such that said interior volume is contractible under the application of an external force against the tapered exterior surface, such that when the staple is placed over the head of the screw, the inner tapered surface of the hole in the staple and the exterior surface of the rod receiving member nest against one another, and only the upper portion of the rod receiving member extends fully through the throughhole, and the upwardly extending annular rim of the throughhole extends above the lower channel surface of the rod receiving channel such that a rod placed in the rod receiving channel seats on the annular rim;

whereby the insertion of the screw into a vertebral bone, the placement of the head into the interior volume of the rod receiving member, the placement of the staple over the rod receiving member such that the vertebral bone fixation protuberances are inserted into the vertebral bone, the placement of the rod in the rod receiving channel and onto the annular rim of the throughhole of the staple, and the application of the first means of securing the rod in the rod receiving channel causes the screw, the rod receiving member, the staple, the vertebral bone and the rod to be locked together in a fully secured combination.

7. A vertebral body screw and staple assembly for use with orthopedic rod implantation apparatus, comprising:

a vertebral body staple having a throughhole formed in a flat surface thereof, the surface of said hole being tapered;

a vertebral body screw having a shaft and a curvate head portion, a rod receiving member having a rod receiving channel and a slotted lower portion having a contractible interior volume into which the head portion of the screw may be inserted and loosely retained;

means for securing a rod in said rod receiving channel;

said staple being mountable about the lower portion of the rod receiving member such that rod receiving channel partially extends through the throughhole, whereby the insertion of a rod in said rod receiving channel, and the application of said means for securing the rod in the rod receiving channel causes the tapered surface of said hole to engage the lower portion of the rod receiving member and cause the contraction of the interior volume thereof, thus locking the screw, the rod receiving member, the staple, and the rod together in a fully secured combination.

\* \* \* \* \*